329-171
4/12/83    XR    4,379,637    SR

United States Patent [19]
Schmid

[11] 4,379,637

[45] Apr. 12, 1983

[54] RADIATION MEASURING APPARATUS

[75] Inventor: Carl J. Schmid, Port Washington, N.Y.

[73] Assignee: Peerless Electronics Research Corp., Commack, N.Y.

[21] Appl. No.: 262,174

[22] Filed: May 11, 1981

Related U.S. Application Data

[63] Continuation-in-part of Ser. No. 15,943, Feb. 28, 1979, Pat. No. 4,273,449.

[51] Int. Cl.³ .................. G01N 21/85; G02B 27/14
[52] U.S. Cl. ........................... 356/411; 250/204; 350/171; 356/410
[58] Field of Search ............... 356/402, 405–425, 356/432–442, 319–321; 350/171; 250/204

[56] References Cited

U.S. PATENT DOCUMENTS

| | | | |
|---|---|---|---|
| 2,339,053 | 1/1944 | Coleman | 356/333 |
| 2,692,527 | 10/1954 | Wethel et al. | 356/152 |
| 2,797,149 | 6/1957 | Skeggs | 23/230 R |
| 2,803,752 | 8/1957 | Warren | 356/435 |
| 2,933,293 | 4/1960 | Ferrari, Jr. | 366/106 |
| 3,016,800 | 1/1962 | Pliskin | 350/266 |
| 3,218,908 | 11/1965 | Armington | 350/174 |
| 3,342,019 | 9/1967 | Smythe | 55/189 |
| 3,572,994 | 3/1971 | Hochstrasser | 356/72 X |
| 3,583,813 | 6/1971 | Shibata et al. | 250/226 X |
| 3,599,630 | 8/1971 | Sato et al. | 128/6 |
| 3,658,422 | 4/1972 | Wilkinson | 356/321 |
| 3,746,429 | 7/1973 | Spindel et al. | 350/266 |
| 4,070,111 | 1/1978 | Harrick | 356/308 |
| 4,273,449 | 6/1981 | Schmid | 356/411 |

FOREIGN PATENT DOCUMENTS 1155846  10/1963   Fed. Rep. of Germany.

OTHER PUBLICATIONS

Smith, Warren J., "Modern Optical Engineering", McGraw-Hill, New York, 1966, pp. 84–96.

*Primary Examiner*—Bruce Y. Arnold
*Attorney, Agent, or Firm*—Lee C. Robinson, Jr.

[57] ABSTRACT

A colorimeter in which a light source, a collimating lens and a band pass filter are supported by a housing that is movable with respect to a stationary beam dividing assembly in a direction at least substantially transverse to the optical axis of the light from the source. The assembly separates the incoming collimated and filtered light into a sample beam and a reference beam which are directed back toward the housing in directions parallel to the optical axis. The movement of the housing toward or away from the sample produces an increase or decrease in the intensity of the light illuminating the sample and a corresponding decrease or increase in the intensity of the light at the reference detector. The arrangement is such that the apparatus may be readily adjusted to obtain accurate colorimeter readings even for samples having abnormally high or low density characteristics.

18 Claims, 7 Drawing Figures

RADIATION MEASURING APPARATUS

CROSS-REFERENCE TO RELATED APPLICATION

This is a continuation-in-part of copending U.S. application Serial No. 15,943 filed Feb. 28, 1979 by Carl Julius Schmid now U.S. Pat. No. 4,273,449, granted June 16, 1981.

BACKGROUND OF THE INVENTION

This invention relates to radiation measuring apparatus and more particularly to apparatus for measuring a particular characteristic of a sample.

The present invention, while of general application, is particularly well suited for use in the quantitative analysis of blood or other body fluids. As is well known, for diagnostic purposes a plurality of samples of body fluid, flowing as serial segments in a stream spaced apart by bubbles of air or other inert fluid, commonly are individually and serially treated with one or more reagents to form a stream having an optical density at a particular wavelength which is indicative of a quantitative characteristic of the sample. In some cases, for example, the reagent comprises an acid solution having a distinct color which reacts with any glucose in the sample to produce a decrease in the density of the color proportional to the amount of glucose. The decrease in density is measured by a colorimeter, and the value is recorded in, say, milligrams of glucose per 100 milliliters of solution.

Heretofore, radiation measuring apparatus of the foregoing type exhibited certain disadvantages. As an illustration, in many such prior apparatus difficulties were encountered in cases in which a particular sample being analyzed exhibited high density and hence reduced the intensity of the radiation to be measured to a level below that at which accurate measurements could be obtained. Variations in the intensity of the radiation source for the apparatus also adversely affected the accuracy of the detected measurements. In addition, and this has been of special moment in cases in which the apparatus was arranged to provide direct readings of the concentration of a substance in the sample, it often was difficult heretofore to calibrate the response of the apparatus so that a given known standard solution resulted in a response at the proper position on the output scale. Furthermore, the measuring apparatus previously employed often were comparatively bulky and exhibited difficulties in the measurement of successive samples on a continuous and trouble-free basis.

SUMMARY

One general object of this invention, therefore, is to provide a new and improved apparatus for measuring radiation representative of a particular characteristic of a sample.

More specifically, it is an object of this invention to provide such radiation measuring apparatus in which accurate measurements are obtained even for samples having abnormally high or low densities.

Another object of the invention is to provide radiation measuring apparatus of the character indicated in which the detected measurements are substantially independent of the intensity of the radiation source.

A further object of the invention is to provide radiation measuring apparatus which may be readily calibrated in accordance with the desired output scale.

Still another object of the invention is to provide radiation measuring apparatus which is compact in size.

A still further object of the invention is to provide radiation measuring apparatus which is economical to manufacture and thoroughly reliable in operation.

In one illustrative embodiment of the invention, the apparatus includes an incandescent lamp or other source of visible or invisible radiation and suitable optics for receiving radiation from the source and directing it along an optical axis. First and second optical systems are disposed in spaced relationship with each other on opposite sides of this axis. A sample holder, illustratively in the form of a conduit or tube containing a continuously flowing sample stream, is located in position to receive radiation from the first optical system. A selected, almost monochromatic portion of the radiation from the source is directed through a radiation dividing assembly, and a part of the radiation then proceeds through the first optical system to the sample in the form of a sample beam. The beam passes through the sample to modify the intensity of the beam in accordance with the optical density of the sample. The intensity of the beam emerging from the sample is detected to produce an output signal representative of the sample density.

In accordance with one feature of the invention, the optical axis of the radiation approaching the dividing assembly may be shifted in a manner which changes the intensity of the radiation reaching the sample. The intensity of the radiation may be readily adjusted with respect to a known standard to provide extremely accurate density measurements even for highly dense or dilute sample materials.

In accordance with another feature of the invention, in certain particularly important embodiments, the radiation dividing assembly serves as a beam divider to separate the received radiation from the source into the sample beam and a reference beam which is directed through the second optical system. The apparatus is provided with first and second detectors for respectively detecting the intensities of these beams, and the signals from the detectors are compared by a ratio detector to produce an output signal which is independent of the intensity of the radiation source.

In accordance with still another feature of several preferred embodiments of the invention, the first and second optical systems are located on opposite sides of the optical axis of the radiation approaching the dividing assembly. The radiation source and the directing optics are supported in a unitary housing which is movable in a direction at least substantially transverse to the axis. The movement of the housing toward and away from the optical systems simultaneously changes the intensities of both the sample beam and the reference beam. As the housing is moved away from the first optical system, for example, the intensity of the radiation reaching the sample is decreased and the intensity of the radiation reaching the reference detector is increased, while movement of the housing in the opposite direction increases the intensity of the radiation reaching the sample and decreases the intensity of the reference beam radiation. The apparatus is extremely compact and may be readily calibrated in accordance with the color density of the particular sample being analyzed.

DESCRIPTION OF CERTAIN PREFERRED EMBODIMENTS

Figure 1:
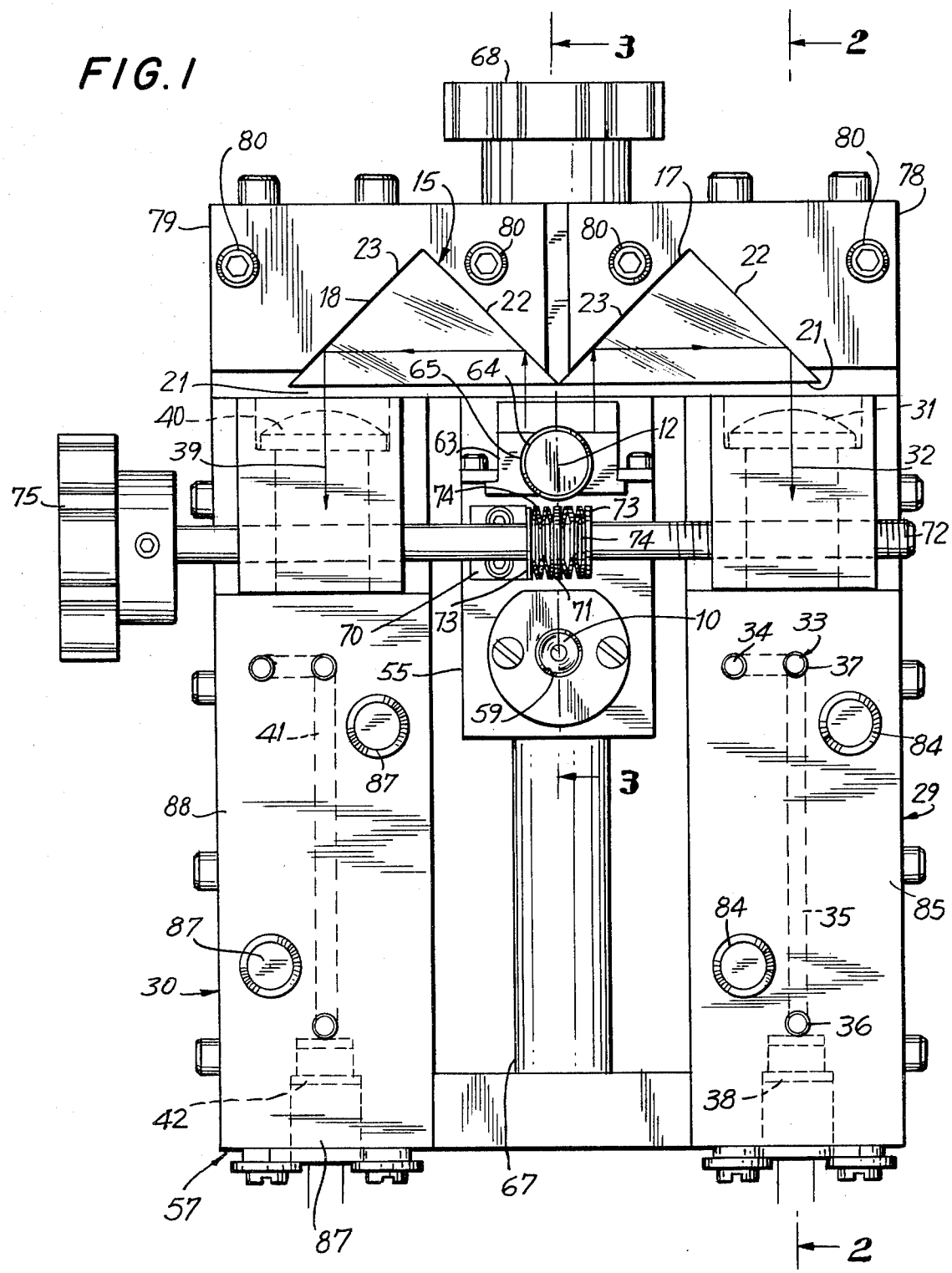
FIG. 1 is a top plan view of radiation measuring apparatus in accordance with one illustrative embodiment of the invention.

Referring to FIGS. 1–5 of the drawings, there is shown radiation measuring apparatus in the form of a colorimeter having an incandescent lamp or other suitable light source 10. As used herein, the term "light" includes not only visible light but also radiation having wavelengths longer and shorter than the visible spectrum. Light from the source 10 is directed along an optical axis indicated generally at 12. The light along the axis 12 proceeds through a collimating lens 13 (FIG. 3) to form parallel rays and then through a band pass filtering lens 14. The band pass filtering lens 14 operates in known manner to permit light having only selected wavelengths to proceed along the axis 12.

The light from the band pass filtering lens 14 is received by a stationary beam dividing assembly 15. The assembly 15 includes two equilateral prisms 17 and 18 which each have three flat faces 21, 22 and 23. The prisms 17 and 18 are arranged in abutting relationship with each other with their faces 21 in a single plane perpendicular to the optical axis 12. The faces 22 and 23 are silvered or otherwise provided with a suitable reflective coating. With this arrangement, the prisms divide the light received from the source 10 into two distinct and separate beams, for purposes that will become more fully apparent hereinafter.

Figure 5:
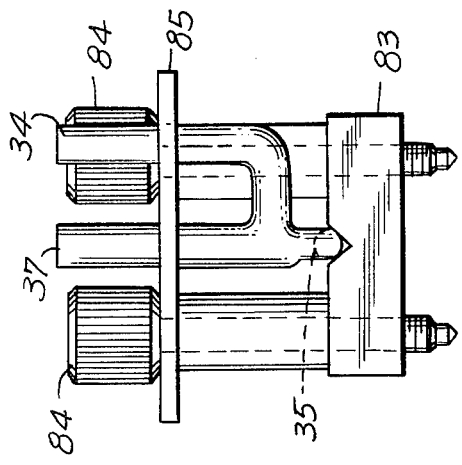
FIG. 5 is an end elevational view of a sample holder for the apparatus of FIG. 1.

A sample optical system 29 and a reference optical system 30 are disposed in spaced relationship with each other on opposite sides of the axis 12 in position to receive radiation from the dividing assembly 15. The sample optical system 29 includes a focusing or condenser lens 31 (FIG. 2) which receives a selected, substantially monochromatic portion of the spectra from the prism 17. The lens 31 forms a sample beam 32 which extends in a direction parallel to the axis 12 and illuminates a sample of material within a sample holder 33. The sample holder 33 is in the form of a U-shaped transparent conduit or tube having an upstanding inlet section 34, a central section 35 in coaxial relationship with the sample beam 32, and an upstanding outlet section 36. In addition, as best seen in FIG. 5, an upstanding bleed tube 37 communicates with the central section 35 at its intersection with the inlet section 34.

The inlet section 34 of the sample holder 33 is arranged to receive a continuous stream of segmented liquid samples which have been treated with suitable reagents to produce a particular color characteristic, the density of which is proportional to the amount by weight of a given substance in the sample solution. One illustrative apparatus for supplying the segmented fluid stream to the sample holder is disclosed in U.S. Pat. No. 4,233,001 issued Nov. 11, 1980 to Carl Julius Schmid. The intensity of the beam of radiation passing through the sample is reduced as a logarithmic function of the sample density and is detected by a photoelectric cell 38 disposed along the axis of the sample beam 32 in juxtaposition with the sample holder 33.

In a similar manner, the reference optical system 30 receives a reference beam 39 in the form of a selected, substantially monochromatic portion of the spectrum of the beam from the prism 18. The configuration and arrangement of the prisms 17 and 18 is such that the wavelengths of the sample and reference beams are the same. The reference system 30 includes a focusing or condenser lens 40 which focuses the received beam on one end of a light pipe 41. The pipe 41 is axially aligned with the reference beam 39 and serves to direct the incoming light to a photoelectric cell 42. The intensity of the light detected by the cell 42 is proportional to that of the light source 10 at the selected wavelength.

Figure 6:
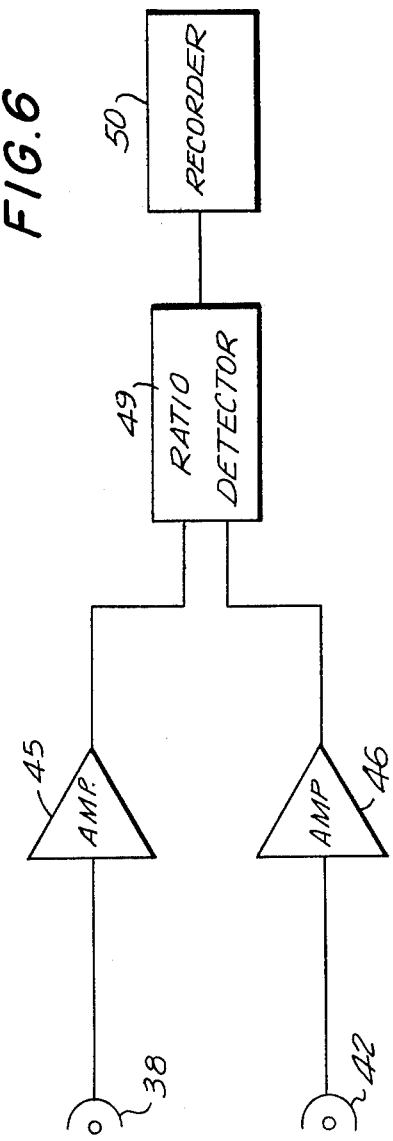
FIG. 6 is a schematic block diagram of an electrical circuit useful with the apparatus.

As best shown in FIG. 6, the sample photocell 38 and the reference photocell 42 are respectively connected to log amplifiers 45 and 46. The output from the amplifiers 45 and 46 is supplied to a ratio detector circuit 49 which produces an output signal representative of the ratio between the detected intensities of the sample and reference beams. The output signal may be recorded by a suitable strip chart recorder 50. The detector 49 and the recorder 50 are calibrated to provide direct readings of the concentration of a selected substance within each of the successive samples moving through the sample tube 33 (FIG. 2) in, say, milligrams per 100 ml. of solution.

Figure 3:
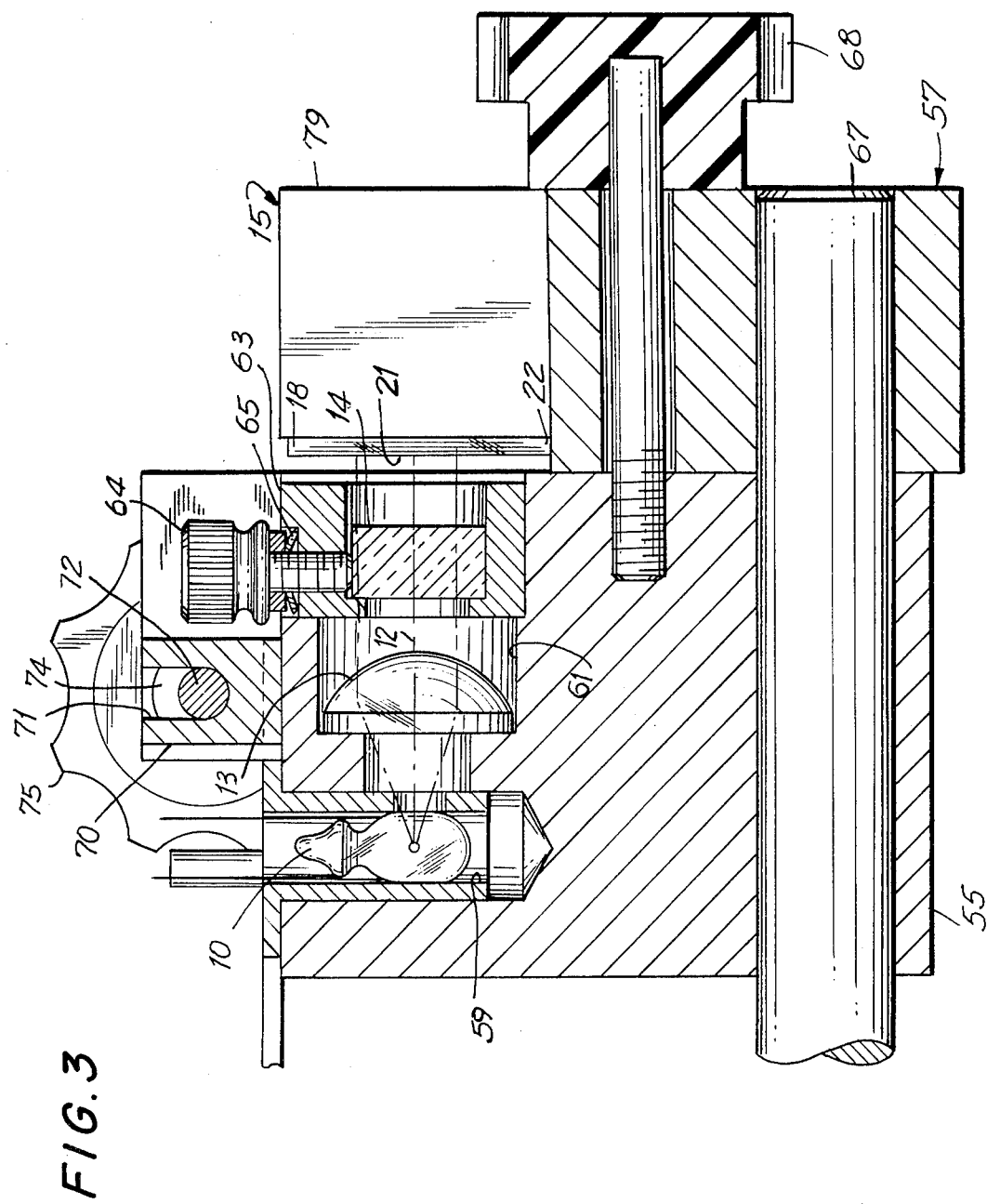
FIG. 3 is an enlarged sectional view taken along the line 3—3 in FIG. 1.
Figure 4:
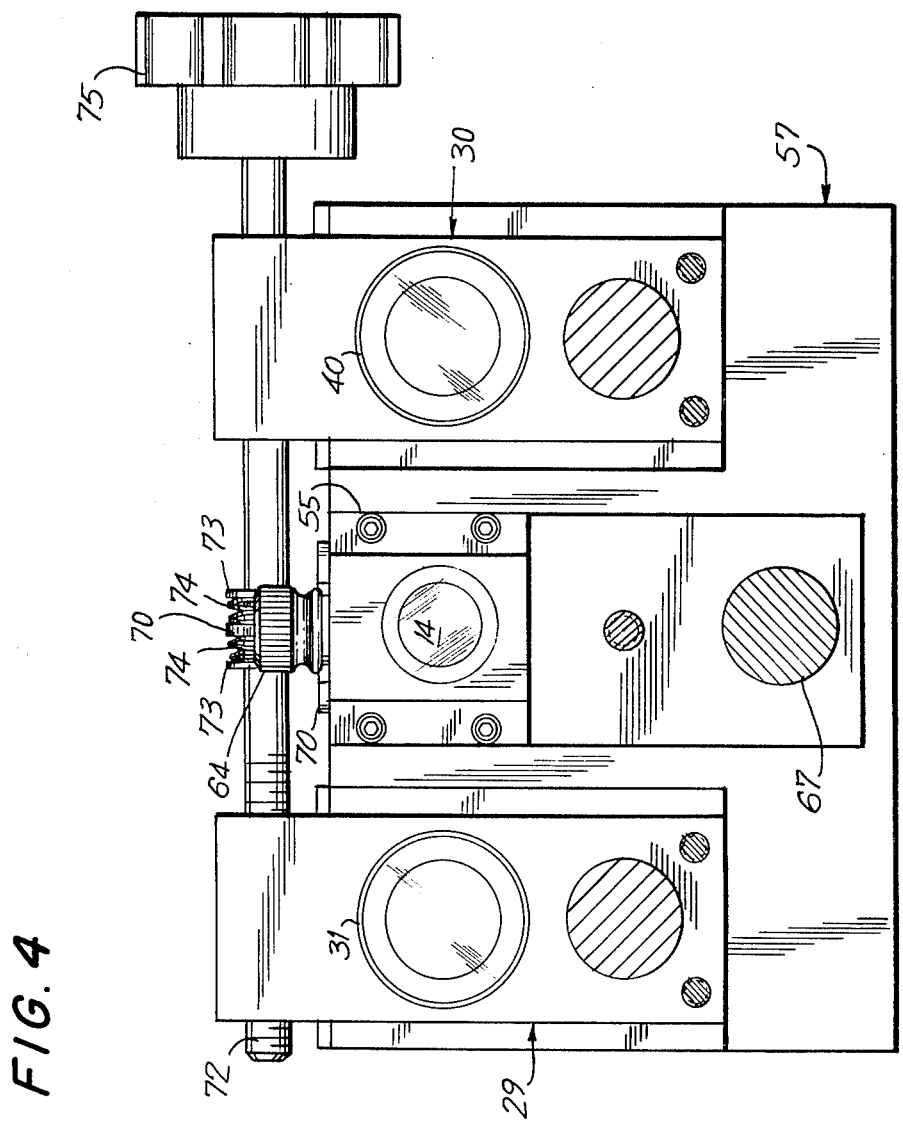
FIG. 4 is an end elevational view of the apparatus of FIG. 1 with certain parts shown in section.

The light source 10, the radiation directing lens 13 and the filter 14 are removably supported within a generally rectangular housing 55 (FIG. 3). The housing 55 in turn is supported by the base member 57 of the apparatus for movement relative thereto in a direction at least substantially transverse to the optical axis 12. The source 10 is disposed within a suitable recess 59 in the upper surface of the housing 55, and the lens 13 is located in a side recess 61 open to the recess 59.

The filter 14 is positioned in a block 63 removably carried by the housing 55. A threaded knob 64 is disposed adjacent the upper surface of the block 63, and a bowed washer 65 is interposed between the knob and the block. Upon the tightening of the knob 64, the washer 65 is compressed and bears against the adjacent portion of the housing 55 to maintain the block 63 and the filter 14 in rigid relationship with the light source 10 and the collimator 13. To remove the filter 14, in order to substitute a different filter or for cleaning purposes, for example, the knob 64 is unscrewed to permit the washer 65 to return to its unbowed condition, and the filter may then be readily lifted from the assembly by means of the knob.

The housing 55 is pivotally supported on the base member 57 by a shaft 67. This shaft extends in a direction parallel to that of the optical axis 12 and is spaced a sufficient distance beneath the light source 10 and the collimating lens 13 that, for practical purposes, the movement of the source and collimator about the shaft is almost linear and is substantially transverse to the axis 12. A knob 68 is located parallel to and immediately above the shaft 67 and serves to maintain the housing 55 in rigid relationship with the base member 57 after the housing has been moved to the desired position.

Extending upwardly from the upper surface of the housing 55 is an angle bracket 70. The bracket 70 is provided with a U-shaped recess 71 which accommodates a threaded rod 72. As best shown in FIG. 1, two retaining rings 73 are affixed to the rod 72 on opposite sides of the bracket 70 and are spaced therefrom by bowed washers 74. Upon the rotation of a control knob 75 affixed to one end of the rod 72, the rings 73 and the washers 74 urge the angle bracket 70 in a direction transverse to the optical axis 12 to similarly move the housing 55, the light source 10, the collimator 13 and the filter 14 relative to the base member 57.

The dividing assembly 15, the sample optical system 29 and the reference optical system 30 are all mounted in a stationary position on the base member 57. The prisms 17 and 18 which comprise the dividing assembly are respectively located in blocks 78 and 79 which are removably secured to the base member 57 by thumb screws 80.

Figure 2:
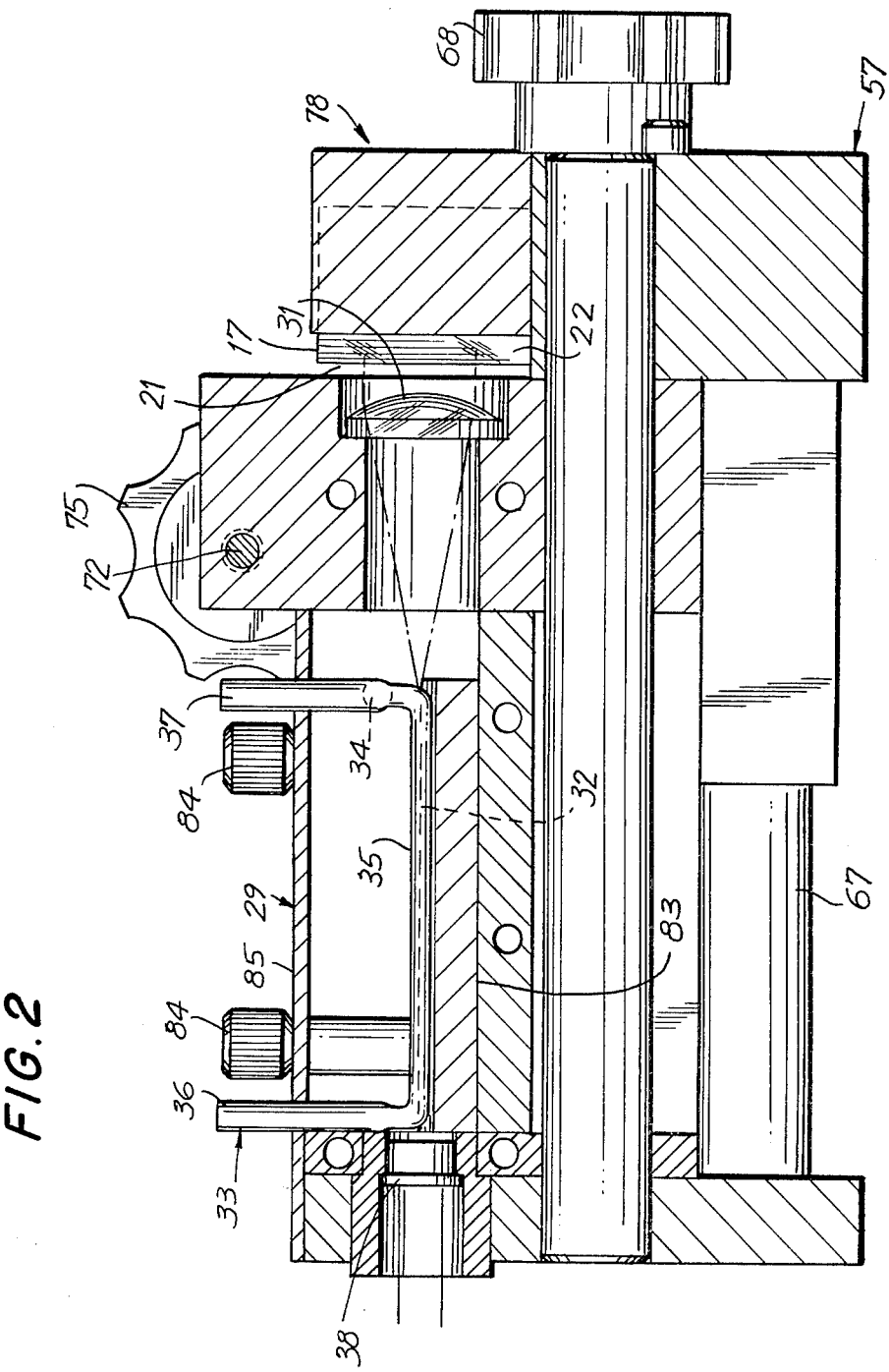
FIG. 2 is a vertical sectional view taken along the line 2—2 in FIG. 1.

As best shown in FIG. 2, the sample holder 33 is supported on a block 83 which also is removably secured to the base member 57 by thumb screws 84. The thumb screws 84 extend through a sample plate 85 and into tapped holes in the block 83 to facilitate the removal of the holder 33. In similar fashion, thumb screws 87 (FIG. 1) extend through a reference plate 88 and into a suitable block (not visible in the drawings) to enable the ready removal of the reference light pipe 41. The sample optical system 29 and the reference optical system 30 are located on opposite sides of the base member 57 such that the sample beam 32 and the reference beam 39 are in parallel equidistant relationship with the optical axis 12 when the axis is at the midpoint of its range.

At the start of the measuring operation, the inlet section 34 of the sample holder 33 is connected to a segmented stream of liquid samples. The stream is pumped into the sample holder 33 through the use of a peristaltic pump such as that disclosed in U.S. Pat. No. 4,233,001 referred to above. As the stream enters the central section 35 of the sample holder, the bleed tube 37 serves to discharge excess fluid and greatly facilitates the realization of a uniform and continuously moving segmented stream which flows through the central section 35 and is discharged from the outlet section 36.

Radiation from the light source 10 is received by the collimating lens 13 and is directed thereby along the optical axis 12 in the form of a beam of radiation having parallel rays. The beam passes through the filter 14 and is separated by the dividing assembly 15 into the substantially monochromatic sample and reference beams 32 and 39. To form the sample beam 32 the incoming radiation undergoes two right-angle reflections by the surfaces 23 and 22 of the prism 17 such that the beam 32 proceeds in a direction opposite to that of the radiation from the source 10 and in parallel relationship with the optical axis 12. The beam 32 is focused by the condenser lens 31 on the adjacent end of the central section 35 of the sample holder 33, and the beam passes through the sample within the section 35 and its intensity is detected by the detector 38.

In a similar manner, the reference portion of the radiation approaching the dividing assembly 15 undergoes successive right-angle reflections by the surfaces 22 and 23 of the prism 18 to form the reference beam 39. The reference beam proceeds in a direction opposite to that of the radiation approaching the assembly 15 and in parallel relationship with the optical axis 12. The condenser lens 40 focuses the reference beam on the adjacent end of the light pipe 41, and the beam proceeds through the pipe and its intensity is detected by the detector 42.

The intensities of the sample and reference beams may be simultaneously changed through the use of the control knob 75 to move the center of the light source 10 in a plane transverse to the optical axis 12. If the density of a particular sample within the sample holder 33 is too high to obtain meaningful measurements, for example, the control knob 75 is adjusted to move the light source housing 55 to the right, as viewed in FIG. 1, away from the reference optical system 30 and toward the sample optical system 29. This movement results in a greater portion of the light from the source 10 being directed toward the sample system 29 by the prism 17 and a correspondingly lesser portion being directed toward the reference system 31 by the prism 18. The intensity of the beam illuminating a sample within the sample holder 33 is accordingly increased to provide an increased output signal at the photocell 38, and there is a corresponding decrease in the intensity of the beam reaching the reference photocell 42.

Conversely, in making measurements of very dilute sample materials, the control knob 75 is adjusted in a direction to move the housing 55 toward the reference optical system 30 and away from the sample optical system 29. This latter movement results in a decrease in the intensity of the light illuminating the sample holder 33 and a corresponding increase in the light reaching the reference detector 42. Through the use of a suitable precalibrated scale for the ratio detector 49 and the recorder 50, the response of the apparatus may be readily adjusted such that a given known standard solution falls on the proper place on the scale. The concentration of successive unknown samples may be read directly from the scale without the need for undertaking further calculations.

Figure 7:
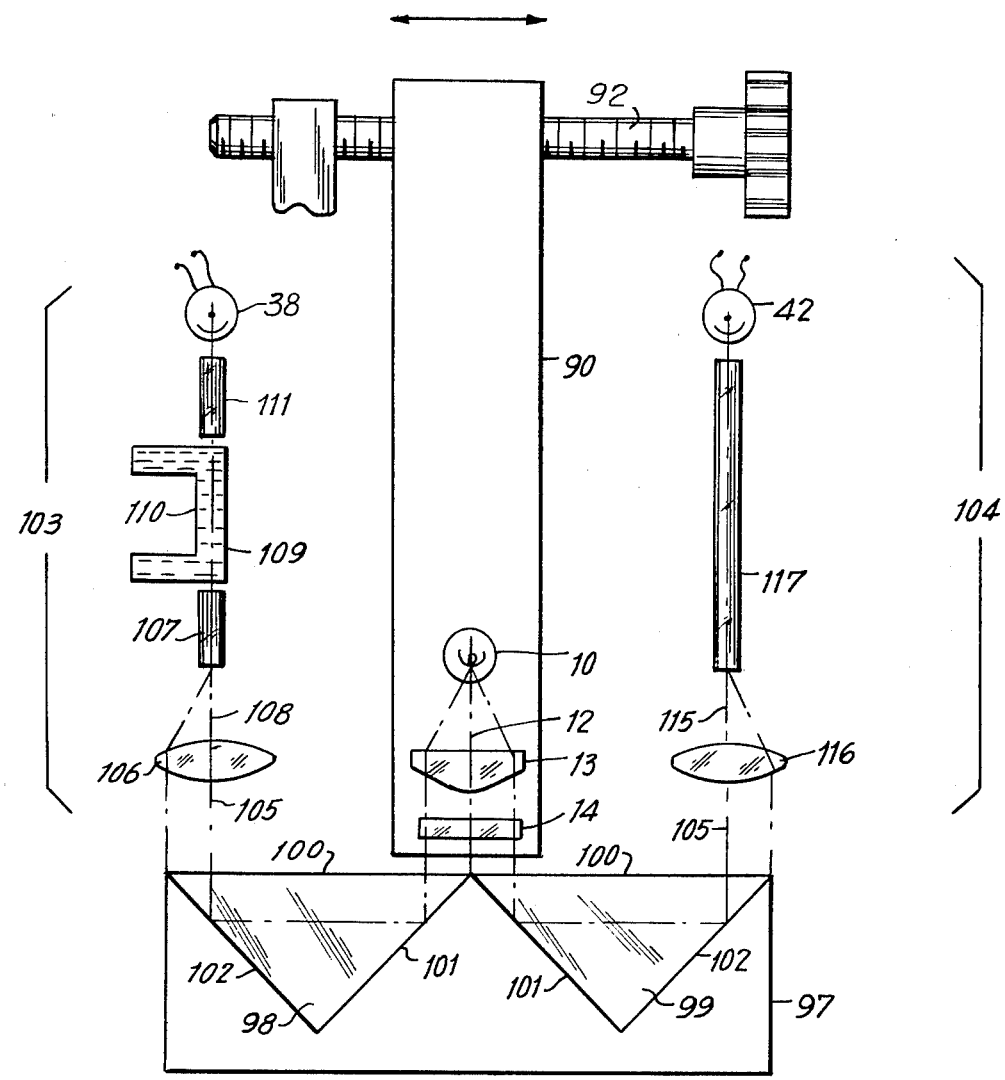
FIG. 7 is a simplified schematic representation of measuring apparatus in accordance with another illustrative embodiment of the invention.

In a number of advantageous arrangements in accordance with the invention, the sample and reference optical systems are positioned along a linear path on opposite sides of the beam divider such that the sample and reference beams are in coaxial relationship with each other. Referring to FIG. 7, for example, the light source 10, the collimating lens 13 and the filter 14 are mounted within a movable housing shown schematically at 90. The light from the source 10 is directed along the optical axis 12 through the lens 13 and the filter 14. The housing 90 is movable in a linear direction perpendicular to the axis 12 by means of a calibrated tracking screw 92. By turning the screw 92, the housing 90 and hence the source 10, the lens 13 and the filter 14 may be moved as a unit relative to the remaining portions of the apparatus.

The filter 14 selects a portion of the light along the optical axis 12 and directs it to a radiation dividing assembly 97. The assembly 97 includes two right prisms 98 and 99 which each have a diagonal face 100 and two right angle faces 101 and 102. The prisms 98 and 99 are arranged with their faces 100 extending in spaced planes perpendicular to the optical axis 12 and their faces 101 in abutting relationship at a 45° angle to the optical axis. The faces 101 and 102 are silvered or otherwise provided with a suitable reflective coating. In the position shown the faces 100 are in one plane which meets the axis 12 at a right angle. With this arrangement, the reflective faces 101 divide the monochromatic light received from the source 10 into two distinct and separate beams.

A sample optical system 103 and a reference optical system 104 are disposed in spaced relationship with each other on opposite sides of the axis 12 in position to receive radiation from the dividing assembly 97. The optical systems 103 and 104 and the dividing assembly 97 are in optical alignment with each other along a linear optical path 105 which is parallel to the axis 12.

The sample optical system 103 includes a focusing lens 106 which receives the portion of the monochromatic light reflected by the face 102 of the prism 98. The received light is focused on one end of a tube or light pipe 107 in coaxial relationship with the optical path 105. The lens 106 forms a sample beam 108 which proceeds through the light pipe 107 and illuminates a sample of material within a tubular sample holder 109. The sample holder 109 is of transparent material but is provided with an opaque coating 110 to prevent the escape of light passing through the sample. A second light pipe 111 is located along the path 105 between the sample holder 109 and the detector 38.

In a similar manner, the reference optical system 104 receives a reference beam 115 in the form of the portion of the monochromatic light reflected by the face 102 of the prism 99. The reference system 104 includes a focusing lens 116 which focuses the received beam on one end of a light pipe 117. The pipe 117 is axially aligned with the optical path 105 and serves to direct the incoming light to the reference detector 42.

The intensities of the sample beam 108 and the reference beam 115 are detected by the respective detectors 38 and 42 to provide an output signal at the ratio detector 49 (FIG. 6) and the recorder 50 in the manner described heretofore. The position of the housing 90 relative to the beam dividing assembly 97 is readily adjustable through the use of the tracking screw 92 to move the radiation directing components within the housing in a plane transverse to the optical axis 12 and thereby divide the light from the source 10 into sample and reference beams of different intensities. In a manner similar to that described heretofore with respect to the embodiment of FIGS. 1–5, the movement of the housing toward or away from the sample optical system 103 produces an increase or decrease in the intensity of the light illuminating the sample and a corresponding decrease or increase in the intensity of the light at the reference detector.

The use of the light pipes 107 and 111 in the sample optical system 103 serves to adapt the apparatus to different size sample holders depending upon the characteristics of the sample and the particular type of measurements being made. In cases in which a sample holder having a shorter central section than that of the sample holder 33 is employed in the apparatus of FIG. 2, for example, a light pipe may be inserted at one or both ends of the central section in axial alignment therewith.

In some embodiments of the invention a second sample holder may be substituted for the light pipe in the reference optical system. The second holder is supplied with a stream of segmented samples, and the intensity of the stream is detected by the detector 42 in a manner similar to that described above.

In each of the illustrated embodiments flat mirrors may be substituted for the prisms in the beam dividing assembly. In the embodiment of FIGS. 1–5 the mirrors are oriented in a manner similar to that of the surface 23 of the prism 17 and the surface 22 of the prism 18, and additional flat mirrors are employed at the locations of the surface 22 of the prism 17 and the surface 23 of the prism 18. In the embodiment of FIG. 7 the mirrors are oriented in a manner similar to that of the prism surfaces 100. A more detailed discussion of the use of mirrors in apparatus of this type appears in U.S. patent application Ser. No. 15,943 referred to heretofore.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. Apparatus for measuring a characteristic of a sample, the apparatus comprising, in combination:
   a source of radiation;
   means for receiving radiation from said source and directing the same along an optical axis;
   housing means supporting the radiation directing means for movement in a direction at least substantially transverse to said optical axis;
   radiation dividing means disposed in a stationary position along said optical axis for separating radiation from said radiation directing means into separate beams;
   an optical system located in spaced relationship with said optical axis for receiving one of said beams;
   a sample holder in position to receive said one beam from said optical system;
   a detector for receiving said one beam from the sample holder and for detecting the intensity of the received beam; and
   means for moving the housing means in said substantially transverse direction to move said radiation directing means toward and away from said optical system and thereby change the intensity of said one beam.

2. Apparatus as defined in claim 1, in which the sample holder includes a sample conduit for continuously receiving successive samples to be analyzed and a bleed conduit communicating with the sample conduit.

3. Apparatus for measuring a characteristic of a sample, the sample comprising, in combination:
   a source of radiation;
   means for receiving radiation from said source and directing the same along an optical axis;
   means located along said optical axis for permitting radiation having only selected wavelengths to proceed along said axis;
   housing means supporting the radiation receiving and directing means for movement in a direction at least substantially transverse to said optical axis;
   radiation dividing means disposed in a stationary position along said optical axis for separating the selected portion of the radiation into separate beams;
   an optical system located in spaced relationship with said optical axis for receiving one of said beams;
   a sample holder in position to receive said one beam from said optical system;

a detector for receiving said one beam from the sample holder and for detecting the intensity of the received beam; and means for moving the housing means in said substantially transverse direction to move said radiation receiving and directing means toward and away from said optical system and thereby to change the intensity of said one beam.

4. Apparatus for measuring a characteristic of a sample, the apparatus comprising, in combination:

a source of radiation;

means for receiving radiation from said source and directing the same along an optical axis;

housing means supporting the source of radiation and the radiation directing means for movement in a direction at least substantially transverse to said optical axis;

radiation dividing means disposed in a stationary position along said optical axis for separating radiation from said radiation receiving and directing means into separate beams, the dividing means directing the beams back toward said radiation receiving and directing means in directions parallel to said optical axis;

an optical system located in spaced relationship with said optical axis for receiving one of said beams;

a sample holder in position to receive said one beam from said optical system;

a detector for receiving said one beam from the sample holder and for detecting the intensity of the received beam; and means for moving the housing means in said substantially transverse direction to move said source of radiation and said radiation receiving and directing means toward and away from said optical system and thereby to change the intensity of said one beam, the movement of the source of radiation and the radiation receiving and directing means away from said optical system decreasing the intensity of the radiation reaching said sample, and the movement of the source of radiation and the radiation receiving and directing means toward said optical system increasing the intensity of the radiation reaching said sample.

5. Apparatus for measuring a characteristic of a sample, the apparatus comprising, in combination:

a source of radiation;

means for receiving radiation from said source and directing the same along an optical axis;

filtering means located along said optical axis for permitting radiation having only selected wavelengths to proceed along said axis;

housing means supporting the source of radiation, the radiation receiving and directing means and the filtering means for movement in a direction substantially transverse to said optical axis;

radiation dividing means disposed in a stationary position along said optical axis for separating the selected portion of the radiation into separate beams;

an optical system located in spaced relationship with said optical axis for receiving one of said beams;

a sample holder in position to receive said one beam from said optical system;

a detector for receiving said one beam from the sample holder and for detecting the intensity of the received beam; and means for moving the housing means in said substantially transverse direction in order to move said housing means, said source of radiation, said radiation receiving and directing means and said selecting means toward and away from said optical system and thereby change the intensity of said one beam, the movement of the housing means away from said optical system decreasing the intensity of the radiation reaching said sample, and the movement of the housing means toward said optical system increasing the intensity of the radiation reaching said sample.

6. Apparatus as defined in claim 5, which further comprises at least one light pipe disposed along the path of said one beam.

7. Apparatus for measuring a characteristic of a sample, the apparatus comprising, in combination:

a source of radiation;

means for receiving radiation from said source and directing the same along an optical axis;

housing means supporting the radiation receiving and directing means for movement in a direction substantially transverse to said optical axis;

radiation dividing means disposed in a stationary position along said optical axis for separating radiation from said radiation receiving and directing means into separate beams;

first and second optical systems located on opposite sides of said optical axis for respectively receiving said beams;

a sample holder in position to receive the beam from the first optical system;

first and second detectors for respectively receiving the beam from the sample holder and the beam from the second optical system and for detecting the intensities of the received beams; and means for moving the housing means in said substantially transverse direction to move said radiation receiving and directing means toward and away from said optical systems and thereby simultaneously to change the intensities of both of said beams.

8. Apparatus for measuring a characteristic of a sample, the apparatus comprising, in combination:

a source of radiation;

means for receiving radiation from said source and directing the same along an optical axis;

housing means supporting the radiation receiving and directing means for movement in a direction at least substantially transverse to said optical axis;

radiation dividing means disposed in a stationary position along said optical axis for separating radiation from said radiation receiving and directing means into sample and reference beams;

first and second optical systems located on opposite sides of said optical axis for respectively receiving said sample and reference beams;

a sample holder in position to receive the sample beam from the first optical system;

first and second detectors for respectively receiving the sample beam from the sample holder and the reference beam from the second optical system and for detecting the intensities of the received beams; and means for moving the housing means in said substantially transverse direction to move said radiation receiving and directing means toward and away from said optical systems and thereby simultaneously to change the intensities of both the sample beam and the reference beam.

9. Apparatus as defined in claim 8, in which the radiation dividing means directs the sample and reference beams back toward said radiation receiving and directing means in directions parallel to said optical axis.

10. Apparatus as defined in claim 8, in which the radiation dividing means comprises a pair of prisms.

11. Apparatus for measuring a characteristic of a sample, the apparatus comprising, in combination:
a source of radiation;
means for receiving radiation from said source and directing the same along an optical axis;
means located along said optical axis for permitting radiation having only selected wavelengths to proceed along said axis;
housing means supporting the radiation receiving and directing means for movement in a direction substantially transverse to said optical axis;
radiation dividing means disposed in a stationary position along said optical axis for separating the selected portion of the radiation into sample and reference beams;
first and second optical systems located on opposite sides of said optical axis for respectively receiving said sample and reference beams;
a sample holder in position to receive the sample beam from the first optical system;
first and second detectors for respectively receiving the sample beam from the sample holder and the reference beam from the second optical system and for detecting the intensities of the received beams; and
means for moving the housing means in said substantially transverse direction to move said radiation receiving and directing means toward and away from said optical systems and thereby simultaneously to change the intensities of both the sample beam and the reference beam, the movement of the radiation receiving and directing means away from said first optical system decreasing the intensity of the radiation reaching said sample and increasing the intensity of the radiation reaching said second detector, and the movement of the radiation receiving and directing means away from second optical system increasing the intensity of the radiation reaching said sample and decreasing the intensity of the radiation reaching said second detector.

12. Apparatus as defined in claim 11, in which said sample and reference beams are in coaxial relationship with each other.

13. Apparatus as defined in claim 12, in which the common axis of said sample and reference beams extends in a direction perpendicular to said optical axis.

14. Apparatus for measuring a characteristic of a sample, the apparatus comprising, in combination:
a source of radiation;
means for receiving radiation from said source and directing the same along an optical axis;
filtering means located along said optical axis for permitting radiation having only selected wavelengths to proceed along said axis;
housing means supporting the source of radiation, the radiation receiving and directing means and the filtering means for movement in a direction at least substantially transverse to said optical axis;
radiation dividing means disposed in a stationary position along said optical axis for separating the selected portion of the radiation into sample and reference beams;
first and second optical systems located on opposite sides of said optical axis for respectively receiving said sample and reference beams;
a sample holder in position to receive the sample beam from the first optical system;
first and second detectors for respectively receiving the sample beam from the sample holder and the reference beam from the second optical system and for detecting the intensities of the received beams; and
means for moving the housing means in said substantially transverse direction to move said housing means, said source of radiation, said radiation receiving and directing means and said selecting means toward and away from said optical systems and thereby simultaneously to change the intensities of both the sample beam and the reference beam, the movement of the housing means away from said first optical system decreasing the intensity of the radiation reaching said sample and increasing the intensity of the radiation reaching said second detector, and the movement of the housing means away from said second optical system increasing the intensity of the radiation reaching said sample and decreasing the intensity of the radiation reaching said second detector.

15. Apparatus for measuring a characteristic of a sample, the apparatus comprising, in combination:
a source of radiation;
means for receiving radiation from said source and directing the same along an optical axis;
filtering means located along said optical axis for permitting radiation having only selected wavelengths to proceed along said axis;
housing means supporting the source of radiation, the radiation directing means and the filtering means for movement in a direction at least substantially transverse to said optical axis;
radiation dividing means disposed in a stationary position along said optical axis for separating the selected portion of the radiation into sample and reference beams, the dividing means directing the sample and reference beams back toward said radiation receiving and directing means in directions parallel to said optical axis;
first and second optical systems located on opposite sides of said optical axis for respectively receiving said sample and reference beams;
a sample holder in position to receive the sample beam from the first optical system;
first and second detectors for respectively receiving the sample beam from the sample holder and the reference beam from the second optical system and for detecting the intensities of the received beams; and
means for moving the housing means in said substantially transverse direction to move said housing means, said source of radiation, said radiation receiving and directing means and said selecting means toward and away from said optical systems and thereby simultaneously change the intensities of both the sample beam and the reference beam, the movement of the housing means away from said first optical system decreasing the intensity of the radiation reaching said sample and increasing the intensity of the radiation reaching said second detector, and the movement of the housing means away from said second optical system increasing the intensity of the radiation reaching said sample and decreasing the intensity of the radiation reaching said second detector.

16. Apparatus for measuring a characteristic of a sample, the apparatus comprising, in combination:
a source of radiation;
means for receiving radiation from said source and directing the same along an optical axis;
filtering means located along said optical axis for permitting radiation having only selected wavelengths to proceed along said axis;
housing means supporting the source of radiation, the radiation receiving and directing means and the filtering means for movement in a direction at least substantially transverse to said optical axis;
radiation dividing means disposed in a stationary position along said optical axis for separating the selected portion of the radiation into substantially monochromatic sample and reference beams, the dividing means directing the sample and reference beams back toward said directing means in directions parallel to said optical axis;
first and second optical systems located on opposite sides of said optical axis for respectively receiving said sample and reference beams;
a sample holder in position to receive the sample beam from the first optical system, the sample holder including a sample conduit for receiving successive samples to be analyzed and a bleed conduit communicating with the sample conduit;
first and second detectors for respectively receiving the sample beam from the sample holder and the reference beam from the second optical system and for detecting the intensities of the received beams; and
means for moving the housing means in said substantially transverse direction in order to move said housing means, said source of radiation, said radiation receiving and directing means and said selecting means toward and away from said optical systems and thereby simultaneously to change the intensities of both the sample beam and the reference beam, the movement of the housing means away from said first optical system decreasing the intensity of the radiation reaching said sample and increasing the intensity of the radiation reaching said second detector, and the movement of the housing means away from said second optical system increasing the intensity of the radiation reaching said sample and decreasing the intensity of the radiation reaching said second detector.

17. Apparatus as defined in claim 16, in which the sample holder is of U-shaped configuration and is removably disposed in said housing.

18. Apparatus as defined in claim 16, which further comprises means including a bowed washer, for removably maintaining said filtering means in said housing.

* * * * *